(12) United States Patent
Ida et al.

(10) Patent No.: US 10,507,524 B2
(45) Date of Patent: Dec. 17, 2019

(54) METALLIC COPPER DISPERSION, METHOD FOR MANUFACTURING SAME, AND USAGE FOR SAME

(71) Applicant: Ishihara Sangyo Kaisha, Ltd., Osaka (JP)

(72) Inventors: Kiyonobu Ida, Yokkaichi (JP); Mitsuru Watanabe, Yokkaichi (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/907,010

(22) PCT Filed: Jul. 24, 2014

(86) PCT No.: PCT/JP2014/069577
§ 371 (c)(1),
(2) Date: Jan. 22, 2016

(87) PCT Pub. No.: WO2015/012356
PCT Pub. Date: Jan. 29, 2015

(65) Prior Publication Data
US 2016/0167130 A1  Jun. 16, 2016

(30) Foreign Application Priority Data

Jul. 25, 2013  (JP) ................................. 2013-154054

(51) Int. Cl.
| | | |
|---|---|---|
| *B22F 1/00* | (2006.01) | |
| *A01N 25/34* | (2006.01) | |
| *A01N 25/26* | (2006.01) | |
| *B22F 1/02* | (2006.01) | |
| *B22F 9/24* | (2006.01) | |
| *A01N 59/20* | (2006.01) | |
| *C09D 5/14* | (2006.01) | |
| *C09D 5/24* | (2006.01) | |
| *C09D 133/08* | (2006.01) | |

(52) U.S. Cl.
CPC ............ *B22F 1/0022* (2013.01); *A01N 25/26* (2013.01); *A01N 25/34* (2013.01); *A01N 59/20* (2013.01); *B22F 1/02* (2013.01); *B22F 9/24* (2013.01); *C09D 5/14* (2013.01); *C09D 5/24* (2013.01); *C09D 133/08* (2013.01); *B22F 2009/245* (2013.01); *B22F 2301/10* (2013.01); *B22F 2302/45* (2013.01); *B22F 2304/054* (2013.01); *B22F 2304/056* (2013.01)

(58) Field of Classification Search
CPC ................................. A01N 25/26; A01N 59/20
See application file for complete search history.

(56) References Cited

U.S. PATENT DOCUMENTS

| | | |
|---|---|---|
| 2008/0148904 A1 | 6/2008 | Tomonari et al. |
| 2011/0155432 A1 | 6/2011 | Tomonari et al. |

FOREIGN PATENT DOCUMENTS

| | | | |
|---|---|---|---|
| JP | 2012023014 | | 2/2012 |
| JP | 2012-241213 A | | 12/2012 |
| JP | 2012241213 A | * | 12/2012 |
| WO | WO2006/019144 A1 | | 2/2006 |
| WO | WO2010/024385 A1 | | 3/2010 |

OTHER PUBLICATIONS

Office Action issued in Japanese patent application No. 2015-528335, Feb. 2, 2018, pp. 1-4, translation pp. 1-5.

* cited by examiner

*Primary Examiner* — Kyle A Purdy
(74) *Attorney, Agent, or Firm* — Jeffrey S. Melcher; Melcher Patent Law PLLC

(57) ABSTRACT

The purpose of the present invention is to provide a metallic copper dispersion: capable of maintaining dispersion stability of metallic copper particles for a long period of time; suitable for inkjet printing, spray coating, or the like; and capable of allowing a metallic copper-containing film having an excellent electrical conductivity and metallic color tone to be manufactured in a simple manner by performing low-temperature heating or plasma irradiation after application. The metallic copper dispersion is a dispersion containing at least an organic solvent, a polymer dispersant, and metallic copper particles having gelatin on the particle surface, wherein the metallic copper particles in the dispersion have a cumulative 50% particle size (D50) of 1-130 nm and a cumulative 90% particle size (D90) of 10-300 nm, and the polymer dispersant has an amine number of 10-150 mgKOH/g. The metallic copper dispersion is manufactured by reducing copper oxide in an aqueous solvent in the presence of gelatin, then performing solid-liquid separation, and then mixing the obtained metallic copper particles having gelatin on the particle surface and the polymer dispersant into the organic solvent.

26 Claims, No Drawings

METALLIC COPPER DISPERSION, METHOD FOR MANUFACTURING SAME, AND USAGE FOR SAME

This application is the national phase of international application PCT/JP2014/069577 filed 24 Jul. 2014 which designated the U.S.

TECHNICAL FIELD

The present invention relates to a metallic copper dispersion liquid blending metallic copper particles; a process for preparing the metallic copper dispersion liquid; an electrode, a wiring pattern, and a coating film which are formed using the metallic copper dispersion liquid; a decorative article and a antimicrobial article which form the coating film thereon; and further a process for producing a metallic copper-containing film used for them.

BACKGROUND ART

A dispersion liquid blending metallic copper particles is a general term that usually includes compositions, such as coating agents, paints, pastes, and inks, which is obtained by dispersing metallic copper particles in solvent, and further blending therein an additive such as a binder, a dispersant, and a viscosity modifier when necessary. Such a dispersion liquid is used, by taking advantage of the characteristics of the metallic copper particles, in various applications such as applications to secure electrical conduction, applications to prevent electrification, applications to shield electromagnetic waves, applications to give metallic luster or antibacterial properties. Additionally, metallic copper particles having an average particle diameter of about 1 to 200 nm have been used in recent years as the metallic copper particles which are blended, and its applications have been expanding to various fields. Specifically, the metallic copper particles are used, by taking advantage of a high electrical conductivity thereof, for electromagnetic wave shielding of transparent members such as a cathode-ray tube and a liquid crystal display. Moreover, technique of forming a fine electrode or a fine circuit-wiring pattern by the use of the metallic copper particles of nanomaterials has been proposed. This technique is as follows: the dispersion liquid blending the metallic copper particles coats a substrate to form an electrode pattern or circuit-wiring pattern by a coating method such as a screen printing or inkjet printing, and thereafter the metallic copper particles are fused by heating at a relatively low temperature. This technique has been applied particularly to production of printed wiring boards. Furthermore, the fusion of the metallic copper particles easily progresses to exhibit metallic luster even under the conditions of a mild heating, and thus the dispersion liquid blending the metallic copper particles has been attracting attention in design and decoration applications as a simple technique for producing a mirror surface.

Regarding metallic copper particles or a dispersion liquid dispersing the metallic copper particles, Patent Literature 1 for example discloses that the metallic copper particles are obtained by mixing a divalent copper oxide and a reducing agent in a liquid medium in the presence of a complexing agent and a protective colloid to reduce the divalent copper oxide, and that the obtained metallic copper particles are dispersed in a dispersion medium to make a fluid composition, and also discloses that a water solvent, hydrophilic organic solvents, hydrophobic organic solvents, and the like are used as the dispersion medium. Moreover, Patent Literature 2 describes a dispersion liquid containing the metallic copper particles having gelatin on the surfaces of the particles, a polymeric dispersant, and an organic solvent, wherein the gelatin has a difference between an amine value and an acid value (amine value–acid value) of 0 or less and the polymeric dispersant has a difference between an amine value and an acid value (amine value–acid value) of 0 to 50.

CITATION LIST

Patent Literature

Patent Literature 1: WO 2006/019144 A1
Patent Literature 2: WO 2010/024385 A1

SUMMARY OF INVENTION

Technical Problem

The metallic copper particles described in Patent Literature 1 are excellent in the dispersion stability, and are heat-meltable at a relatively low temperature, and therefore is preferably used in various applications such as applications to secure electrical conduction, applications to prevent electrification, applications to shield electromagnetic waves, applications to give metallic lusters or antibacterial properties. However, the dispersion liquid in which printability and coatability of the metallic copper particles when used in an inkjet printing, spray coating, or the like can be further improved, and of which dispersion stability can keep for a long period of time was desired. Therefore, in Patent Literature 2, the particular gelatin is used as protective colloid, and when the metallic copper particles having the gelatin on the surfaces of the particles are dispersed in the organic solvent, the particular polymeric dispersant that compensates the difference between the amino value and acid value of the gelatin is used as the dispersant. This metallic copper dispersion liquid in Patent Literature 2 is excellent in the printability and the like, and is also excellent in the dispersion stability. However, a dispersion liquid capable of providing the film-forming at the further lower temperature, furthermore the dispersion liquid capable of providing the film-forming within the further shorter time, and technical means for achieving them have been desired.

Solution to Problem

The present inventors conducted diligent studies to solve the above problems, and have found that it is important to make an aggregation diameter (90% cumulative particle diameter) of the metallic copper particles small by adding a polymeric dispersant having a particular amine value thereto. Moreover, as a result of focusing on thermal properties of the polymeric dispersant, specifically focusing on the specific heat capacity, the glass transition temperature, and the like, the present inventors have found that it is preferable to blend a polymeric dispersant having a specific heat capacity of 1.0 to 2.0 J/(g·K) at the glass transition point, and that thereby, the film-forming at the further lower temperature and film-forming by light irradiation, plasma irradiation, or the like become possible due to the good dispersion stability of the metallic copper particles and the small specific heat capacity of the dispersant. Furthermore, the present inventors have found that it is more preferable that the polymeric dispersant have a glass transition point within a range of −70 to 10° C., and that the metallic copper dispersion liquid is prepared by the steps of: reducing copper oxide in the presence of gelatin in an aqueous solvent; thereafter performing solid-liquid separation; and subsequently mixing metallic copper particles having the gelatin on the surfaces thereof, obtained by the solid-liquid separation, with a polymeric dispersant in an organic solvent. As a result, the present inventors have finally completed the present invention.

Namely, the present invention is:

(1) a metallic copper dispersion liquid containing at least metallic copper particles having gelatin on surfaces thereof, a polymeric dispersant, and an organic solvent, in which the polymeric dispersant has an amine value of 10 to 150 mgKOH/g, and the metallic copper particles have a 50% cumulative particle diameter (D50) of 1 to 130 nm and a 90% cumulative particle diameter (D90) of 10 to 300 nm;

(2) the metallic copper dispersion liquid according to (1), in which the polymeric dispersant has a specific heat capacity of 1.0 to 2.0 J/(g·K) at a glass transition point of the polymeric dispersant;

(3) a process for preparing a metallic copper dispersion liquid, including the steps of:

reducing copper oxide in the presence of gelatin in an aqueous solvent, thereafter performing solid-liquid separation, and subsequently mixing and dispersing metallic copper particles having the gelatin on surfaces thereof, obtained by the solid-liquid separation with a polymeric dispersant in an organic solvent, wherein the polymeric dispersant has an amine value of 10 to 150 mgKOH/g, and the metallic copper particles have a 50% cumulative particle diameter (D50) of 1 to 130 nm and a 90% cumulative particle diameter (D90) of 10 to 300 nm;

(4) the process for preparing a metallic copper dispersion liquid according to (3), in which the polymeric dispersant having a specific heat capacity of 1.0 to 2.0 J/(g·K) at a glass transition point of the polymeric dispersant is used, and (5) a process for producing a metallic copper-containing film including a step (a) of adhering the metallic copper dispersion liquid onto a surface of a base material, including a step (b) of heating the metallic copper-containing film produced by the step (a) under a reducing gas atmosphere, a step (c) of irradiating a whole or one partial region of the metallic copper-containing film produced by the step (a) with light, or a step (d) of irradiating a whole or one partial region of the metallic copper-containing film produced by the step (a) with plasma.

Advantageous Effects of Invention

Because the metallic copper dispersion liquid according to the present invention blends a particular polymeric dispersant, the metallic copper dispersion liquid has a small aggregation diameter (D90) of the metallic copper particles to provide excellent dispersion stability, and makes it possible to further lower the heating temperature needed to form a film. Moreover, the film-forming is also possible by light irradiation, plasma irradiation, or the like. Therefore, the metallic copper-containing film excellent in electrical conductivity and metallic color tone can be easily produced by coating the surface of a base material with the metallic copper dispersion liquid according to the present invention or by performing the heating, light irradiation, plasma irradiation, or the like after being coated with the metallic copper dispersion liquid according to the present invention.

For these reasons, the metallic copper dispersion liquid according to the present invention is used as materials to secure electrical conduction, materials to prevent electrification, materials to shield electromagnetic waves, materials to give metallic luster or antibacterial properties, and the like, and is used particularly in applications to form a fine electrode and a fine circuit-wiring pattern, such as a print wiring board making use of the electrical conductivity of the metallic copper-containing film, and in design and decoration uses making use of metallic color tone of the metallic copper-containing film.

DESCRIPTION OF EMBODIMENTS

The present invention is a dispersion liquid of which metallic copper particles are dispersed in an organic solvent, the dispersion liquid containing at least the metallic copper particles having gelatin on surfaces thereof, a polymeric dispersant, and an organic solvent, and the dispersion liquid includes compositions generally called as dispersants, coating agents, paints, pastes, inks, or the like. The metallic copper particles used in the present invention have gelatin, which is mentioned later, existing on the surfaces of the particles, and can be arbitrarily selected depending on intended uses without particular limitations of the particle diameter of the metallic copper particles, the constituents other than copper, and the like. With respect to the particle diameter of the metallic copper particles, it is preferable to arbitrarily use the metallic copper particles of which an average particle diameter is about 1 nm to 100 nm in terms of easiness of availability, and it is more preferable to use the metallic copper particles having an average particle diameter about 1 to 70 nm. It is still more preferable to use the metallic copper particles having an average particle diameter of about 1 to 50 nm because such metallic copper particles can be used in applications of various fields, and in order to obtain a finer electrode or a finer circuit-wiring pattern, it is still more preferable to use the metallic copper particles having an average particle diameter in a range of 1 to 30 nm. The metallic copper particles may include impurities inevitable on the production process such as oxygen and a dissimilar metal, or the metallic copper particles may contain oxygen, a metal oxide, an organic compound such as a complexing agent, or the like in advance when necessary in order to prevent a rapid oxidation of the metallic copper particles.

Also, for the purpose of further lowering the heating temperature needed in the film-forming and for the purpose of preventing rapid oxidation, an alloy of copper with a dissimilar metal may be formed in the metallic copper particles, or the surfaces of the metallic copper particles may be coated with a dissimilar metal or an alloy of copper with a dissimilar metal. Such copper alloy particles, or metallic copper particles or metallic copper alloy particles covered with the metal or alloy are also included in the metallic copper particles according to the present invention. As the dissimilar metal, metals such as silver, gold, bismuth, tin, nickel, zinc, and lead can be used, and the content amount and the coating amount can be arbitrarily set.

The particle size distribution of the metallic copper particles in the dispersion is an important factor for the formation of a film. When the particle diameters at 50% accumulation and at 90% accumulation are measured, the metallic copper particles whose particle diameters are small are preferable, and particularly the metallic copper particles whose aggregation diameters represented by D90 are small are preferable. The polymeric dispersant is arbitrarily selected so that the 50% cumulative particle diameter and 90% cumulative particle diameter can be within a particular range. The 50% cumulative particle diameter (D50) of the metallic copper particles is preferably 1 to 130 nm, more preferably 10 to 120 nm, and still more preferably 20 to 100 nm. Moreover, the 90% cumulative particle diameter (D90) of the metallic copper particles is preferably 10 to 300 nm, more preferably 40 to 250 nm, and still more preferably 60 to 200 nm. Furthermore, the 10% cumulative particle diameter (D10) of the metallic copper particles is preferably 0.5 to 100 nm, more preferably 1 to 80 nm, and still more preferably 5 to 70 nm. The 50% cumulative particle diameter (which is also referred to as D50, median diameter, or cumulative median diameter), 90% cumulative particle diameter (D90), and 10% cumulative particle diameter (D10) of the metallic copper particles dispersed in a dispersion liquid are measured with an apparatus for measuring the particle size distribution by a dynamic light scattering method. And, when an SD value is calculated from these values using the following equation 1, the SD value is preferably 0.6 to 3.5, more preferably 0.6 to 3.0, still more preferably 0.7 to 2.5, and particularly preferably 1.0 to 2.5.

$$SD \text{ value} = (D90 - D10)/D50 \qquad \text{Equation 1:}$$

Gelatin exits on surfaces of the metallic copper particles. The gelatin includes not only gelatin in the state as extracted but also the compound obtained by hydrolyzing this gelatin to lower the molecular weight (which is, hereinafter, sometimes referred to as hydrolyzed gelatin or collagen peptide) and the compounds obtained by chemically modifying them (which are, hereinafter, sometimes referred to as modified gelatin). In general, gelatin is an animal protein obtained from collagen as a parental material. In the production process of the gelatin, pretreatment of raw materials is performed with the inorganic acid such as hydrochloric acid or sulfuric acid, or lime in order to efficiently extract high-quality gelatin from raw materials such as cattle bones, cattle hides, and pig hides. The gelatin obtained through the pretreatment with the inorganic acid is called acid-treated gelatin and the gelatin obtained from the pretreatment with the lime is called alkali-treated (or lime-treated) gelatin. During the process for extracting gelatin, an acid amide in collagen is hydrolyzed and releases ammonia to change into a carboxyl group, and therefore the isoionic point of the gelatin is lowered. Because particularly the alkali-treated gelatin is deamidated to nearly 100% in a liming process, the isoionic point is in an acidic region, and pH thereof is nearly 5. On the other hand, because the acid-treated gelatin provides a low deamidation ratio due to the shortness of a raw material treatment period, the isoionic point is in an alkaline region, and pH thereof is about 8 to about 9 near the isoionic point of collagen. For these reasons, the gelatin has an amine value because of having a basic group and a hydroxy group, and has an acid value because of having an acidic group. The gelatin existing on the surfaces of the metallic copper particles in the present invention is preferably the alkali-treated gelatin, and the difference between the amine value and the acid value measured by the method as will be mentioned later, namely (amine value−acid value), is preferably 0 or less, and more preferably the range of −50 to 0. Compared with the acid-treated gelatin, the alkali-treated gelatin exhibits high effects as protective colloid of the metallic copper particles, and thus is preferable.

Moreover, the collagen peptide (hydrolyzed gelatin) is, directly or through gelatin, obtained by hydrolyzing collagen (collagen protein) included in animal bones and skins by means of an enzyme, acid, alkali, or the like. The conventionally-known methods can be used as a hydrolysis method for obtaining collagen peptide (hydrolyzed gelatin). For example, hydrolysis can be performed by means of a method using an enzyme, a method using a chemical treatment with an acid or alkali, or the like. As to the enzyme, any enzyme may be used as long as it has a function of cleaving a peptide bond of gelatin. The enzyme is usually called a proteolytic enzyme or protease. The specific examples include a collagenase, a thiol protease, a serine protease, an acidic protease, an alkaline protease, and a metal protease, and one of them may be singularly used, or two or more of them may be used in combination. Examples of the thiol protease include plant-derived thiol proteases such as a chymopapain, a papain, a promelain, a ficin, an animal-derived cathepsin, and a calcium-dependent protease. Examples of the serine proteases include trypsin and cathepsin D. Examples of the acid protease include hepsin and chymosin. When the enzyme is used, it is preferable to use 0.01 to 5 parts by mass of the enzyme based on 100 parts by mass of the gelatin before the hydrolysis treatment, and it is preferable that the temperature condition of the hydrolysis is 30 to 70° C. and the treatment time of the hydrolysis is 0.5 to 24 hours. When the hydrolysis treatment is performed with the enzyme, deactivation of the enzyme is performed after the treatment. The deactivation of enzyme is performed by heating, and the heating temperature is, for example, 70 to 100° C.

When the acid or alkali is used, it is preferable to set the pH of the gelatin solution to 3 or less, or 10 or more, and it is preferable that the temperature condition of the hydrolysis is 50 to 90° C. and the treatment time of the hydrolysis is 1 to 8 hours. Examples of the acid include hydrochloric acid, sulfuric acid, nitric acid, and the like. Examples of the alkali include sodium hydroxide, calcium hydroxide, and the like. When the hydrolysis is performed with the acid or alkali, the desalination is performed by means of neutralization with a neutralizing agent or by means of an ion exchange resin. At the time when the hydrolysis treatment is completed, the hydrolyzed gelatin is dissolved or dispersed in the hydrolysis treatment solution. The various purification treatments which are usually used can be applied to this solution. The purification treatment is not particularly limited. For example, activated carbon can be added to improve tone of color or textures, or remove impurities, or the conventionally-known solid-liquid separation treatment such as a filtration or centrifugal separation can be used to remove impurities.

The modified gelatin may be obtained by chemically modifying gelatin, namely, by chemically modifying a side chain of each amino acid residue, a terminal amino group, a terminal carboxyl group, or the like, contained in gelatin. For example, by chemically modifying the side chain of amino acid residues contained in the gelatin to introduce a functional group containing nitrogen element, such as an amino group, an imino group, a cyano group, an azo group, an azi group, a nitrile group, an isonitrile group, a diimide group, a cyano group, an isocyanate group, and a nitro group; a functional group containing sulfur element, such as a thiol group, sulfone group, a sulfide group, and a disulfide group; and a functional group containing both the nitrogen element and the sulfur element, such as a thioisocyanate group and a thioamide group, and further coordinating the kinds and amounts of the functional groups to be introduced, the average particle diameter of the metallic copper particles to be obtained can be controlled to have various levels.

As a general chemical modification method, for example, the method having the steps of: adding a water-soluble carbodiimide to a gelatin solution to activate a carboxyl group contained in gelatin; and then reacting an arbitrary amino compound with the activated carboxyl group to amidate the gelatin can be used. By using this method, an amino acid containing a sulfur element, such as methionine, or an amino acid containing a nitrogen element, such as lysine, can be easily introduced, for example. Examples of the water-soluble carbodiimide include 1-ethyl-3-(3-dimethylaminopropyl)carbodiimide (EDC), 1-cyclohexyl-3-(2-morpholinyl-4-ethyl)carbodiimide p-toluenesulfonic acid salt (CMC), N,N'-dicyclohexylcarbodiimide (DCC), and the like. The gelatin that is applicable to the present invention may be gelatin obtained by performing the hydrolysis treatment and the chemical modification. In this case, the chemical modification may be performed after the hydrolysis treatment, or the hydrolysis treatment may be performed after the chemical modification.

In the present invention, the average particle diameter of the metallic copper particles can be controlled by selecting whether the size of the average molecular weight of the gelatin is large or small. In this case, regardless of the measurement methods of the average molecular weight such as the mass average molecular weight and the number average molecular weight, any measurement methods can be used as the judgment standard on whether the size of the average molecular weight of the gelatin is large or small. Specifically, taking the mass average molecular weight as an example, the mass average weight of the gelatin is preferably 2000 to 200000. Also, taking the number average molecular weight as an example, the number average molecular weight of the gelatin is preferably 200 to 60000. By the range of such an average molecular weight, it is possible to avoid the following problems: the problem that when the average molecular weight is too small, there is a risk that the gelatin does not sufficiently function as protective colloid; and the problem that when the average molecular weight is too large, there are risks that the control of the average particle diameter becomes difficult and the content of organic components in the protective colloid becomes too large. The mass average molecular weight of the gelatin is more preferably 150000 or less, still more preferably 100000 or less, and particularly preferably 5000 to 20000. Also, the number average molecular weight of the gelatin is more preferably 50000 or less, still more preferably 30000 or less, and particularly preferably 500 to 20000. In this way, the reasons why the hydrolyzed gelatin of which the molecular weight is lowered by the hydrolysis is preferable is because by using such a gelatin, the variation of the particle diameter distribution of the metallic copper particles to be obtained becomes small, and is also because the sintering at a lower temperature upon preparing a metallic copper-containing film becomes possible.

(Measurement of Molecular Weight of Gelatin)

The "average molecular weight" in the present invention is a value measured by a "PAGI method". The "PAGI method" here is a method for estimating the molecular weight distribution by determining a chromatogram of a sample solution by a gel filtration using a high-performance liquid chromatography. Specifically, the average molecular weight was measured by the following method. In a 100 mL measuring flask, 2.0 g of a sample was placed, an eluent consisting of a mixed solution of equal amounts of 0.1 M potassium dihydrogen phosphate and 0.1 M disodium hydrogen phosphate was added thereto, then the sample was expanded for 1 hour; the resultant was heated at 40° C. for 60 minutes to dissolve the sample, and then the resulting eluent was diluted accurately 10 times after cooling to room temperature, and thus the resultant solution was used as a test liquid. The chromatogram of the test liquid was determined by the following gel filtration method. Columns: Shodex Asahipak GS 620 7G installed in tandem with another one was used. By using flow rate: 1.0 mL/min, column temperature: 50° C., measurement wavelength: 230 nm, and pullulan (P-82, manufactured by SHOWA DENKO K.K.) of which the molecular weight is known, the elution time was determined, and thereby a calibration curve was made. Thereafter, the gelatin was analyzed, and the mass average molecular weight and number average molecular weight of this specimen were determined using the following equation. In the following equation, Si represents absorbance at each point, and Mi represents a molecular weight at elution time Ti.

Mass average molecular weight=(ΣSi×Mi)/ΣSi

Number average molecular weight=ΣSi/(ΣSi/Mi)

In the present invention, the gelatin exists on the surfaces of the metallic copper particles. However the gelatin has a high acid value, and therefore the metallic copper particles having the gelatin dissociate in a solvent to be electrically negative and are easy to aggregate in an organic solvent. Thus, the polymeric dispersant is mixed to neutralize acid sites which cause an acid value of the gelatin. The polymeric dispersant as well as gelatin contain a hydroxy group, an acidic group, a basic group, and the like, and therefore has an amine value and an acid value, and the amine value of the polymeric dispersant is preferably 10 to 150 mgKOH/g, more preferably 10 to 130 mgKOH/g, still more preferably 10 to 90 mgKOH/g, particularly preferably 15 to 80 mgKOH/g, and most preferably 15 to 50 mgKOH/g. The amine value of the above ranges is preferable in terms of the contribution to the dispersion stability of the metallic copper particles in an organic solvent.

Moreover, with respect to the amine value and acid value of the polymeric compound, it is preferable that the polymeric compound have an amine value (base site) and an acid value (acid site) in an amount which is equal to or more than the amount that compensates (neutralizes) the amine value and acid value of the gelatin that exists on the surfaces of the metallic copper particles, and the difference between the amine value and the acid value, namely (amine value−acid value) is preferably the range of 0 to 50, and more preferably the range of 1 to 30. The polymeric dispersant may be electrostatically coupled to the base site or acid site of the gelatin through the base site or acid site thereof. For the above reasons, (amine value of polymeric dispersant×mass of polymeric dispersant)−(acid value of gelatin×mass of gelatin) is considered as being preferably 0 or more.

The specific heat capacity of the polymeric dispersant at the glass transition point is preferably 1.0 to 2.0 J/(g·K), because the heat accumulation amount of the polymeric dispersant is small to make the heat amount necessary for raising a temperature by 1 K small and to make the heat amount added for the purpose of the decomposition small, is more preferably in a range of 1.2 to 1.9 J/(g·K), and still more preferably in a range of 1.3 to 1.8 J/(g·K). Moreover, the glass transition point of the polymeric dispersant is preferably in a range of −70 to 10° C. because the glass transition occurs at a low temperature to make the heat amount added for the purpose of the decomposition small, and the glass transition is more preferably in a range of −70 to 7° C., still more preferably in a range of −70 to 5° C., and further more preferably in a range of −70 to 0° C. For the above reasons, in the present invention, a more preferable polymeric dispersant has an amine value of 10 to 90 mgKOH/g and a glass transition point in a range of −70 to 10° C., and a still more preferable polymeric dispersant has an amine value of 10 to 90 mgKOH/g, a glass transition point of −70 to 10° C., and a specific heat capacity of 1.0 to 2.0 J/(g·K) at the glass transition point.

(Measurement of Specific Heat Capacity at Glass Transition Point)

According to JIS K 7123-1987 "Testing Methods for Specific Heat Capacity of Plastics", the specific heat capacity was measured with DSC Q 100 Type manufactured by TA Instruments. With respect to a temperature-raising pattern, the temperature was held at −90° C. for 5 minutes, then raised to 40° C. at 5° C./min, and held at 40° C. for 5 minutes. As analytical software, option software "Thermal Specialty Library" manufactured by TA Instruments was used.

(Measurement of Glass Transition Point)

According to JIS K 7121-1987 "Testing Methods for Transition Temperatures of Plastics", the glass transition point was measured with DSC Q 100 Type manufactured by TA Instruments. With respect to a temperature-raising pattern, the temperature was held at −90° C. for 5 minutes, then raised to 40° C. at 5° C./min, and kept at 40° C. for 5 minutes.

The polymeric dispersant is, for example, a polymer or copolymer having a tertiary amino group, quaternary ammonium, a heterocyclic group having a basic nitrogen atom, or a basic group such as a hydroxyl group, and may have an acidic group such as a carboxyl group, and therefore the amine value and acid value of the polymeric dispersant are compensated, so that the (amine value−acid value) may be 0. The polymeric dispersant having the amine value higher than the acid value is preferable, and the (amine value−acid value) is preferably in a range of 0 to 50, and more preferably in a range of 1 to 30. Because the basic group or acidic group of the polymeric dispersant is a functional group affinitive to the metallic copper particles covered with the gelatin, the polymeric dispersant having one or more basic groups or acidic groups in the main chain and/or the side chain is preferable, and the polymeric dispersant having several basic groups or acidic groups in the main chain and/or the side chain is more preferable. The basic groups or acidic groups may be placed at one terminal of the main chain of the polymer and/or one terminal of the side chain of the polymer. The straight-chain polymers such as A-B block type polymers, polymers having a comb-shaped structure with a plurality of side chains, and the like can be used as the polymeric dispersant.

The mass average molecular weight of the polymeric dispersant is not limited, but the mass average molecular weight measured by a gel permeation chromatography method is preferably in a range of 2000 to 1000000 g/mol. The reasons are because the problem that when the mass average molecular weight is less than 2000 g/mol, the dispersion stability is not sufficient, and the problem that when the mass average molecular weight exceeds 1000000 g/mol, viscosity is too high and handling is likely to be difficult can be avoided thereby. The mass average molecular weight is more preferably in a range of 4000 to 1000000 g/mol, still more preferably in a range of 10000 to 1000000 g/mol, and further more preferably in a range of 1000 to 100000 g/mol. Moreover, it is preferable that the amounts of elements of phosphorus, sodium, and potassium, included in the polymeric dispersant are low, and it is more preferable that these elements are not included in the polymeric dispersant. The reasons are because the problem that when the elements of phosphorus, sodium and potassium are included in the polymeric dispersant, these elements remain as ash in producing an electrode, a wiring pattern, or the like by heating and sintering can be avoided thereby. One or more of such polymeric dispersants can be arbitrarily selected and used.

Specifically, the polymeric dispersant includes polymers having a basic group such as salts of long-chain polyaminoamides and polar acid esters, unsaturated polycarboxylic acid polyaminoamides, polycarboxylic acid salts of polyaminoamides, and salts of long-chain polyaminoamides and acid polymers. Moreover, the polymeric dispersant also includes alkylammonium salts, amine salts, and amide amine salts of polymers such as acrylic polymers, acrylic copolymers, modified polyester acids, polyether ester acids, polyether carboxylic acids, and polycarboxylic acids, and straight-chain type acrylic polymers or straight-chain type acrylic copolymers are preferable. Commercially available polymeric dispersants can also be used as such a polymeric dispersant.

The amine values of the gelatin and the polymeric dispersant denote the total amount of free bases and bases, and expressed by an equivalent amount of potassium hydroxide in mg to the amount of hydrochloric acid needed to neutralize 1 g of a sample. Moreover, the acid value denotes the total amount of free fatty acids and fatty acids, and expressed by an amount of potassium hydroxide in mg needed to neutralize 1 g of a sample. Specifically, the amine value and the acid value are measured by the following method according to JIS K7700 or ASTM D2074 below.

(Method for Measuring Amine Value)

In 300 mL of a mixed solvent of ethanol and pure water, 5 g of the gelatin or polymeric dispersant, and several drops of a bromocresol green ethanol solution are dissolved. Then a 0.1 M HCl ethanol solution whose factor (correction coefficient) has been calculated is added to the resultant mixed solution, and the amine value is calculated from the titer of the 0.1M HCl ethanol solution when yellow of a bromocresol green indicator continues for 30 seconds.

(Method for Measuring Acid Value)

In 300 mL of pure water, 5 g of the gelatin or polymeric dispersant, and several drops of a phenolphthalein solution are dissolved. Then a 0.1M KOH ethanol solution whose factor (correction coefficient) has been calculated is added to the resultant mixed solution. The acid value is calculated from the titer of the 0.1M KOH ethanol solution when light red of a phenolphthalein indicator continues 30 seconds.

The organic solvent can be arbitrarily selected, and specifically, at least one selected from hydrocarbon solvents such as toluene, xylene, solvent naphtha, normal hexane, isohexane, cyclohexane, methylcyclohexane, normal heptane, tridecane, tetradecane, and pentadecane; alcoholic solvents such as methanol, ethanol, butanol, IPA (isopropyl alcohol), normal propyl alcohol, 2-butanol, TBA (tertiary butanol), butanediol, ethylhexanol, and benzyl alcohol; ketone solvents such as acetone, methyl ethyl ketone, methyl isobutyl ketone, DIBK (diisobutyl ketone), cyclohexanone, and DAA (diacetone alcohol); ester solvents such as ethyl acetate, butyl acetate, methoxybutyl acetate, cellosolve acetate, amyl acetate, normal propyl acetate, isopropyl acetate, methyl lactate, ethyl lactate, and butyl lactate; ether solvents such as methyl cellosolve, cellosolve, butyl cellosolve, dioxane, MTBE (methyl tertiary butyl ether), and butyl carbitol; glycol solvents such as ethylene glycol, diethylene glycol, triethylene glycol, and propylene glycol; glycol ether solvents such as diethylene glycol monomethyl ether, triethylene glycol monomethyl ether, propylene glycol monomethyl ether, and 3-methoxy-3-methyl-1-butanol; and glycol ester solvents such as ethylene glycol monomethyl ether acetate, PMA (propylene glycol monomethyl ether acetate), diethylene glycol monobutyl ether acetate, and diethylene glycol monoethyl ether acetate can be used as the organic solvent. The organic solvent having a low viscosity is preferable for adaptation to reduction in viscosity of the metallic copper dispersion liquid, and the organic solvent having a viscosity in a range of 1 to 20 mPa·s is preferable. As such an organic solvent, toluene, butyl carbitol, butanol, propylene glycol-1-monomethyl ether-2-acetate, butyl cellosolve, tetradecane, and the like are suitably used.

It is preferable that the gelatin exists in an amount within a range of about 0.1 to 15 parts by mass based on 100 parts by mass of the metallic copper particles because a desired effect is obtained, and the range is more preferably about 0.1 to 10 parts by mass. The polymeric dispersant is preferably in a range of 0.1 to 20 parts by mass based on 100 parts by mass of the metallic copper particles because a desired effect is obtained. The reasons are because the problem that when the amount of the polymeric dispersant is too much smaller than this range, it is difficult to obtain the effects of the present invention and the problem that when the amount of the polymeric dispersant is too much larger than this range, the electrical conductivity is often obstructed in applications to an electrode material and the cloudiness or the like often occurs to deteriorate an appearance in applications to a decorative article. The more preferable range is 0.1 to 10 parts by mass. The particles which are partially coated with colloid and the particles which are not coated with colloid may be present as long as the effects of the present invention are not obstructed. The concentration of the metallic copper particles in the dispersion liquid can be arbitrarily adjusted, and specifically, the concentration of the metallic copper particles can be adjusted to 10% by mass or more, preferably 10 to 80% by mass, and more preferably about 20 to about 70% by mass.

In the metallic copper dispersion liquid according to the present invention, the metallic copper particles are sufficiently dispersed, and therefore even if the metallic copper particles are in a high concentration, viscosity of the dispersion liquid can be adjusted to be relatively low. For example, the viscosity of the dispersion liquid can be adjusted to preferably 100 mPa·s or less, more preferably 1 to 30 mPa·s, and still more preferably 1 to 20 mPa·s. Moreover, when the concentration of the metallic copper particles in the dispersion liquid is increased, the viscosity of the dispersion liquid is easily increased. However the dispersion liquid according to the present invention can maintain the viscosity even when the concentration of the metallic copper particles is 15% by mass or more. Thus, the dispersion liquid according to the present invention has a low viscosity and a high concentration as described above, and therefore can be suitably used for an ink jet printing, spray coating, or the like. For the above reasons, a preferable embodiment of the metallic copper dispersion liquid according to the present invention is as follow: the concentration of the metallic copper particles is 15% by mass or more; the metallic copper particles have a 50% cumulative particle diameter (D50) of 1 to 130 nm, preferably 10 to 120 nm, and more preferably about 20 to 100 nm, and a 90% cumulative particle diameter (D90) of 10 to 300 nm, preferably 40 to 250 nm, and more preferably about 60 to 200 nm; and the dispersion liquid has a viscosity of 100 mPa·s or less.

Other than the metallic copper particles, the organic solvent and the polymeric dispersant, a curable resin, a thickener, a plasticizer, an antifungal agent, a surface active agent, a non-surface active type dispersant, a surface control agent (leveling agent), and the like can be arbitrarily blended in the metallic copper dispersion liquid according to the present invention when necessary. The curable resin can further improve adhesion of a coating product to a base material. As the curable resin, resins of a dissolved type in a low-polar and non-aqueous solvent, an emulsion type, a colloidal dispersion type, and the like can be used without limitation. Moreover, as a resin kind of the curable resin, the known protein polymers, acrylic resins, polyester resins, urethane resins, cellulose, and the like can be used without limitation. The amount of the curable resin component blended is preferably 10 parts by mass or less based on 100 parts by mass of the metallic copper particles, more preferably 8 parts by mass or less, and still more preferably 5 parts by mass or less. As the surface active agent, cationic surface active agents are preferable, and are compounds having the surface activity in a portion that dissociates in an aqueous solvent to show electrical positivity. Examples of the cationic surface active agent include (1) quaternary ammonium salts ((a) aliphatic quaternary ammonium salts (such as [RN(CH$_3$)$_3$]$^+$X$^-$, [RR'N(CH$_3$)$_2$]$^+$X$^-$, [RR'R"N(CH$_3$)]$^+$X$^-$, and [RR'R"R'"N]$^+$X$^-$: wherein R, R', R", and R'" represent a same or different alkyl group; X represents a halogen atom such as Cl, Br, and I, and hereinafter, as defined above), and (b) aromatic quaternary ammonium salts (such as [R$_3$N(CH$_2$Ar)]$^+$X$^-$ and [RR'N(CH$_2$Ar)$_2$]$^+$X$^-$: wherein Ar represents an aryl group), and (c) heterocyclic quaternary ammonium salts (e.g. pyridinium salts ([C$_6$H$_5$N—R]$^+$X$^-$) and imidazolinium salts ([R—CN(CNR'R")C$_2$H$_4$]$^+$X$^-$)), and (2) alkylamine salts (such as RH$_2$NY, RR'HNY, and RR'R"NY: wherein Y represents an organic acid, an inorganic acid, or the like), and one of them may be used, or two or more thereof may be used. Specifically, the aliphatic quaternary ammonium salts include octyltrimethylammonium chloride, stearyltrimethylammonium chloride, cetyltrimethylammonium chloride, cetyltrimethylammonium bromide, lauryltrimethylammonium chloride, dioctyldimethylammonium chloride, distearyldimethylammonium chloride, trioctylmethylammonium chloride, tristearylmethylammonium chloride, tetraoctylammonium chloride, and the like. The aromatic quaternary ammonium salts include decyldimethylbenzylammonium chloride, lauryldimethylbenzylammonium chloride, stearyldimethylbenzylammonium chloride, benzethonium chloride, and the like. The heterocyclic quaternary ammonium salts include cetylpyridinium chloride, an alkyl isoquinolinium bromide, and the like. The alkylamine salts include neutralized products of octylamine, decylamine, laurylamine, stearylamine, coconut oil amine, dioctylamine, distearylamine, trioctylamine, tristearylamine, and dioctylmethylamine neutralized with an inorganic acid such as hydrochloric acid, nitric acid, and sulfuric acid, or a carboxylic acid such as acetic acid. Alternatively, a neutralized product obtained by reacting a mercapto carboxylic acid on the surfaces of the metallic copper particles and/or a salt thereof with alkylamine may be used as the alkylamine salt. Among the quaternary ammonium salts, those having at least one alkyl group with a number of carbon atoms of 8 or more or benzyl group are particularly preferable, and such quaternary ammonium salts include stearyltrimethylammonium chloride (number of carbon atoms of alkyl group: 18), octyltrimethylammonium chloride (number of carbon atoms of alkyl group: 8), lauryltrimethylammonium chloride (number of carbon atoms of alkyl group: 12), cetyltrimethylammonium chloride (number of carbon atoms of alkyl group: 16), cetyltrimethylammonium bromide (number of carbon atoms of alkyl group: 16), tetraoctylammonium bromide (number of carbon atoms of alkyl group: 8), dimethyltetradecylbenzylammonium chloride (number of carbon atoms of alkyl group: 14), distearyldimethylbenzylammonium chloride (number of carbon atoms of alkyl group: 18), stearyldimethylbenzylammonium chloride (number of carbon atoms of alkyl group: 18), and benzalkonium chloride (number of carbon atoms of alkyl group: 12 to 18). Moreover, among the alkylamines of the alkylamine salts, those having at least one alkyl group with a number of carbon atoms of 8 or more are preferable, and such alkylamines include octylamine (number of carbon atoms of alkyl group: 8), laurylamine (number of carbon atoms of alkyl group: 12), stearylamine (number of carbon atoms of alkyl group: 18), dioctylamine (number of carbon atoms of alkyl group: 8), dilaurylamine (number of carbon atoms of alkyl group: 12), distearylamine (number of carbon atoms of alkyl group: 18), trioctylamine (number of carbon atoms of alkyl group: 8), and trilaurylamine (number of carbon atoms of alkyl group: 12). Moreover, the surface control agent controls the surface tension of an organic solvent dispersion to prevent defects such as cissing and craters, and the surface control agents include acrylic surface control agents, vinyl surface control agents, silicone surface control agents, fluorine surface control agents, and the like. The amount of the surface active agent to be added and the amount of the surface control agent to be used can be arbitrarily adjusted, and for example, the amount is preferably 2.0 parts by mass or less based on 100 parts by mass of the metallic copper particles, and more preferably 0.2 parts by mass or less.

Next, the present invention is a process for producing a metallic copper dispersion liquid, including: reducing copper oxide in the presence of gelatin in an aqueous solvent; thereafter performing solid-liquid separation; and subsequently and subsequently mixing metallic copper particles having the gelatin on the surfaces thereof, obtained by the solid-liquid separation, with a polymeric dispersant in an organic solvent, in which the polymeric dispersant has an amine value of 10 to 150 mgKOH/g, and the metallic copper particles have a 50% cumulative particle diameter (D50) of 1 to 130 nm and a 90% cumulative particle diameter (D90) of 10 to 300 nm.

First of all, when the gelatin is used as protective colloid and further copper oxide and a reducing agent are mixed and reduced under the presence of it in an aqueous solvent, metallic copper particles having the gelatin on the surfaces thereof are produced. By the use of the gelatin, the gelatin exists on the surfaces of the produced metallic copper particles so that the amounts of the aggregates of the metallic copper particles in the aqueous solvent can be small and the metallic copper particles having good dispersibility can be produced. The gelatin having a difference between an amine value and an acid value (amine value–acid value) of 0 or less is preferable, and the gelatin having a difference between the amine value and the acid value in a range of –50 to 0 is more preferable. It is preferable to set the amount of the gelatin to be used in a range of 1 to 100 parts by mass based on 100 parts by mass of the copper oxide because dispersion of the produced copper particles is easily stabilized, a range of 2 to 50 parts by mass is more preferable, and a range of 3 to 15 parts by mass is still more preferable. It is preferable to use a divalent copper oxide as the copper oxide. The "divalent copper oxide" is a copper oxide in which a valence of copper is divalent ($Cu^{2+}$), and includes copper (II) oxide, copper (II) hydroxide, and a mixture thereof. The copper oxide may arbitrarily include impurities such as other metals, metallic compounds, and nonmetallic compounds.

As the reducing agent, it is preferable to use a reducing agent having a strong reducing power so that no monovalent copper oxide occurs and/or remains during the reduction reaction. Examples thereof include hydrazine reducing agents such as hydrazine and hydrazine compounds including hydrazine hydrochloride, hydrazine sulfate, and hydrazine hydrate; sodium borohydride, sodium sulfite, sodium hydrogensulfite, sodium thiosulfate, sodium nitrite, sodium hyponitrate, phosphorous acid and its salts such as sodium phosphite; and hypophosphorous acid and its salts such as sodium hypophosphite. One of these may be used, or two or more thereof may be used. Particularly, the hydrazine reducing agents have a strong reducing power, and are preferable. The amount of the reducing agent to be used can appropriately be set as long as it is an amount by which the copper particles can be produced from the copper oxide, and it is preferable that the amount of the reducing agent to be used be in a range of 0.2 to 5 mol based on 1 mol of copper contained in the copper oxide. The reason is because the problem that when the amount of the reducing agent is smaller than the range, the metallic copper particles cannot be sufficiently produced due to the hardness of the reaction progress and the problem that when the amount of the reducing agent is larger than the range, the desired copper particles are hard to obtain due to the excess of the reaction progress can be avoided. A more preferable amount of the reducing agent to be used is in a range of 0.3 to 2 mol.

The aqueous solvent is a solvent that contains water, and examples thereof include water and a mixed solvent of water and an organic solvent such as alcohol. It is preferable to use an aqueous medium from the industrial viewpoint. The reaction temperature is preferably in a range of 10° C. to the boiling point of a medium to be used because the reaction easily progresses. The reaction temperature is more preferably in a range of 40 to 95° C. because fine metallic copper particles are obtained. The reaction temperature is still more preferably in a range of 60 to 95° C., and particularly preferably in a range of 80 to 95° C. It is preferable to adjust the pH of the reaction liquid in a range of 3 to 12 with an acid or alkali in advance because the precipitation of the copper oxide can be prevented to uniformly perform the reaction. The reaction time can be set by controlling the time and the like to add a raw material such as the reducing agent. For example, the reaction time of a range of about 10 minutes to 6 hours is appropriate.

Moreover, a complexing agent can be also used when necessary at a time of the reduction. It is considered that the complexing agent used when necessary acts in a process in which copper ions are eluted from the copper oxide, or in a process in which the copper oxide is reduced to produce metallic copper. The complexing agent means a compound capable of forming a copper complex compound by coupling of donor atoms in a ligand contained in the complexing agent with copper ions or metallic copper, and examples of the donor atom include nitrogen, oxygen, sulfur, and the like. Specifically, (1) The complexing agents having nitrogen as the donor atom include (a) amines (for example, primary amines such as butylamine, ethylamine, propylamine, and ethylenediamine; secondary amines such as dibutylamine, diethylamine, dipropylamine and imines such as piperidine and pyrrolidine; tertiary amines such as tributylamine, triethylamine, and tripropylamine; and those having two or more primary to tertiary amines in one molecule of diethylenetriamine or triethylenetetramine), (b) nitrogen-containing heterocyclic compounds (for example, imidazole, pyridine, and bipyridine), (c) nitriles (for example, acetonitrile, and benzonitrile) and cyanides, (d) ammonia and ammonium compounds (for example, ammonium chloride, and ammonium sulfate), (e) oximes, and the like.

(2) The complexing agents having oxygen as the donor atom include (a) carboxylic acids (for example, oxycarboxylic acids such as citric acid, malic acid, tartaric acid, and lactic acid; monocarboxylic acids such as acetic acid and formic acid; dicarboxylic acids such as oxalic acid and malonic acid; and aromatic carboxylic acids such as benzoic acid), (b) ketones (for example, monoketones such as acetone, and diketones such as acetylacetone and benzoylacetone), (c) aldehydes, (d) alcohols (such as monohydric alcohol, glycols, and glycerols), (e) quinones, (f) ethers, (g) phosphoric acid (orthophosphoric acid) and phosphoric acid compounds (for example, hexametaphosphoric acid, pyrophosphoric acid, phosphorous acid, and hypophosphorous acid), (h) sulfonic acid or sulfonic acid compounds, and the like.

(3) The complexing agents having sulfur as the donor atom include (a) aliphatic thiols (for example, methyl mercaptan, ethyl mercaptan, propyl mercaptan, isopropyl mercaptan, n-butyl mercaptan, allyl mercaptan, and dimethyl mercaptan), (b) alicyclic thiols (such as cyclohexyl thiol), (c) aromatic thiols (such as thiophenol), (d) thioketones, (e) thioethers, (f) polythiols, (g) thiocarbonic acids (trithiocarbonic acids), (h) sulfur-containing heterocyclic compounds (for example, dithiol, thiophene, and thiopyran), (i) thiocyanates and isothiocyanates, (j) inorganic sulfur compounds (for example, sodium sulfide, potassium sulfide, and hydrogen sulfide), and the like.

(4) The complexing agents having two or more donor atoms include (a) amino acids (donor atoms are nitrogen and oxygen: for example, neutral amino acids such as glycine and alanine; basic amino acids such as histidine and arginine; and acidic amino acids such as aspartic acid and glutamic acid), (b) amino polycarboxylic acids (donor atoms are nitrogen and oxygen: for example, ethylenediaminetetraacetate (EDTA), nitrilotriacetate (NTA), iminodiacetate (IDA), ethylenediaminediacetate (EDDA), ethyleneglycoldiethyletherdiaminetetraacetate (GEDA)), (c) alkanolamines (donor atoms are nitrogen and oxygen: for example, ethanolamine, diethanolamine, and triethanolamine), (d) nitroso compounds and nitrosyl compounds (donor atoms are nitrogen and oxygen), (e) mercaptocarboxylic acids (donors are sulfur and oxygen: for example, mercaptopropionic acid, mercaptoacetic acid, thiodipropionic acid, mercaptosuccinic acid, dimercaptosuccinic acid, thioacetic acid, and thiodiglycolic acid), (f) thioglycols (donors are sulfur and oxygen: for example, mercaptoethanol, and thiodiethylene glycol), (g) thionic acids (donors are sulfur and oxygen), (h) thiocarbonic acids (donor atoms are sulfur and oxygen: for example, monothiocarbonic acid, dithiocarbonic acid, and thione carbonic acid), (i) aminothiols (donors are sulfur and nitrogen: aminoethylmercaptan, thiodiethylamine, and the like), (j) thioamides (donor atoms are sulfur and nitrogen: for example, thioformamide), (k) thioureas (donor atoms are sulfur and nitrogen), (l) thiazoles (donor atoms are sulfur and nitrogen: for example, thiazole, and benzothiazole), (m) sulfur-containing amino acids (donors are sulfur, nitrogen and oxygen: cysteine, methionine, and the like), and the like.

(5) Examples of salts of the above compounds and derivatives thereof include alkali metal salts such as trisodium citrate, potassium sodium tartrate, sodium hypophosphite, and disodium ethylenediaminetetraacetate; and esters of a carboxylic acid, phosphoric acid, and sulfonic acid.

Among these complexing agents, at least one thereof can be used. The appropriate amount of the complexing agent to be used varies depending on a kind of the complexing agent, and the amount of the complexing agent to be used is arbitrarily set according to the kind thereof. By reducing the amount of the complexing agent to be used, primary particles of fine metal particles can be made smaller, and by increasing the amount of the complexing agent to be used, primary particles thereof can be made larger.

In the present invention, the complexing agent containing at least one selected from nitrogen and oxygen as the donor atom is preferable because the effects of the present invention are easily obtained. Specifically, at least one complexing agent selected from amines, nitrogen-containing heterocyclic compounds, nitriles, cyanides, carboxylic acids, ketones, phosphoric acid and phosphoric acid compounds, amino acids, aminopolycarboxylic acids, alkanolamines, salts thereof, or derivatives thereof is more preferable. Among carboxylic acids, oxycarboxylic acids are preferable; among ketones, diketones are preferable; and among amino acids, basic and acidic amino acids are preferable. Further, the complexing agent is preferably at least one complexing agent selected from butylamine, ethylamine, propylamine, dibutylamine, diethylamine, dipropylamine, tributylamine, triethylamine, tripropylamine, imidazole, citric acid or alkali metal salts thereof, acetylacetone, hypophosphorous acid or alkali metal salts thereof, histidine, arginine, ethylenediaminetetraacetate or alkali metal salts thereof, ethanolamine, and acetonitrile. As described above, the amount of the oxygen or nitrogen complexing agent to be used is preferably in a range of 0.01 to 200 parts by mass based on 1000 parts by mass of the copper oxide, more preferably in a range of 0.1 to 200 parts by mass, and still more preferably in a range of 0.5 to 150 parts by mass.

Moreover, in the present invention, the production of the finer copper particles is more easily controlled by using a complexing agent in which at least one of the donor atoms is sulfur, and using the complexing agent in an amount of 0.01 to 2 parts by mass based on 1000 parts by mass of the copper oxide. The complexing agents containing sulfur include the mercaptocarboxylic acids, thioglycols, sulfur-containing amino acids, aliphatic thiols, alicyclic thiols, aromatic thiols, thioketones, thioethers, polythiols, thiocarbonic acids, sulfur-containing heterocyclic compounds, thiocyanates and isothiocyanates, inorganic sulfur compounds, thionic acids, aminothiols, thioamides, thioureas, thiazoles, and salts thereof or derivatives thereof. Among these, thioglycols such as mercaptocarboxylic acids and mercaptoethanol, and sulfur-containing amino acids are preferable because the effects are high. The molecular weight is preferably 200 or less, and more preferably 180 or less. Examples of such a mercaptocarboxylic acid include mercaptopropionic acid (molecular weight of 106), mercaptoacetic acid (molecular weight of 92), thiodipropionic acid (molecular weight of 178), mercaptosuccinic acid (molecular weight of 149), dimercaptosuccinic acid (molecular weight of 180), thiodiglycolic acid (molecular weight of 150), and cysteine (molecular weight of 121), and one or more selected from these can be used. The amount of a mercaptocarboxylic acid to be used is more preferably in a range of 0.05 to 1 part by mass, and still more preferably 0.05 parts by mass or more and less than 0.5 parts by mass.

In the present invention, the order to add each raw material at the time of mixing the copper oxide and the reducing agent is not limited. Examples thereof include, for example, (1) a method for concurrently adding the copper oxide and the reducing agent to an aqueous solvent containing the gelatin, and (2) a method for adding the reducing agent to an aqueous solvent containing the gelatin and the copper oxide. Alternatively, the complexing agent may be added at the time of the reduction, and in this case, examples thereof include (3) a method for concurrently adding the complexing agent and the reducing agent to an aqueous solvent containing the gelatin and the copper oxide, and (4) a method for adding a mixed solution of the complexing agent and the reducing agent to an aqueous solvent containing the gelatin and the copper oxide. Among them, the methods (3) and (4) are preferable because the reaction is easily controlled, and the method (4) is particularly preferable. The copper oxide, the reducing agent, the gelatin, and the complexing agent may be suspended or dissolved in an aqueous solvent in advance before they are used in the reduction reaction. In addition, the "concurrently adding" means a method for separately adding the copper oxide and the reducing agent, or the complexing agent and the reducing agent, at the same time during the reaction, and includes not only continuous addition of both materials during the reaction but also intermittent addition of one or both materials. Moreover, in order to produce alloy particles of copper with dissimilar metal, the dissimilar metal compound is mixed and reduced when the copper oxide is reduced, and thereby the copper alloy particles can be produced. Further, in order to coat the surfaces of the copper particles or copper alloy particles with the dissimilar metal, the intended products can be produced by producing the copper particles or copper alloy particles; then mixing the dissimilar metal compound and the produced copper particles or copper alloy particles; and further reducing the dissimilar metal compound. Also, in order to coat the surfaces of the copper particles or copper alloy particles with the alloy of copper and the dissimilar metal, the intended products can be produced by producing the copper particles or copper alloy particles; then mixing the dissimilar metal compound, the copper compound, and the produced copper particles or copper alloy particles; and further reducing the dissimilar metal compound and the copper compound.

After the metallic copper particles having the gelatin on the surfaces thereof are produced by the above-described method, the metallic copper particles are subjected to solid-liquid separation, and washed to obtain a solid of the metallic copper particles. The method for performing solid-liquid separation is not particularly limited, and methods such as gravity filtration, pressure filtration, vacuum filtration, suction filtration, centrifugal filtration, and natural sedimentation can be used. However from the industrial viewpoint, the pressure filtration, the vacuum filtration, and the suction filtration are preferable, and it is preferable to use a filter such as a filter press and a roll press because the filter has high dehydration ability and can treat in large amounts. Next, the solid of the metallic copper particles may be dried by an ordinary method when necessary. The metallic copper particles are easily oxidized, and therefore it is preferable that drying is performed under an atmosphere of an inert gas such as nitrogen and argon in order to suppress the oxidization. After drying, the metallic copper particles may be ground when necessary.

Next, when the solid or dried product of the metallic copper particles are mixed and dispersed in an organic solvent, it is important to use the polymeric dispersant having an amine value of 10 to 150 mgKOH/g. The preferable polymeric dispersant is as described above. The polymeric dispersant having a specific heat capacity of 1.0 to 2.0 J/(g·K) at the glass transition point is preferable, the glass transition point of the polymeric dispersant is more preferably in a range of −70 to 10° C., and the polymeric dispersant having a straight-chain type acrylic polymer or a straight-chain type acrylic copolymer is more preferable. Moreover, the polymeric dispersant having a mass average molecular weight of 1000 to 100000 g/mol is more preferable. As the organic solvent, those described above can be used. A wet type mixer is used as a mixing method, and, for example, fixed type mixers such as stirrers, spiral type mixers, ribbon type mixers, and fluidizing type mixers; rotary type mixers such as cylindrical mixers and twin cylindrical mixers; wet grinding mills such as sand mills, ball mills, bead mills, colloid mills, and sand grinder mills; shakers such as paint shakers; and dispersion machines such as ultrasonic dispersion machines can be used. By arbitrarily selecting these mixers and arbitrarily setting mixing conditions, mixing time, and a dispersion media, needed to be used, the 50% cumulative particle diameter (D50) and the 90% cumulative particle diameter (D90) of the metallic copper particles described above are adjusted to 1 to 130 nm and 10 to 300 nm, respectively. In this way, the metallic copper dispersion liquid containing the metallic copper particles dispersed in the organic solvent is obtained. Moreover, the metallic copper particles may be, before the mixing, ground when necessary using a grinding mill such as a compression grinding type mill, an impact compression grinding type mill, a shearing grinding type mill, and a friction grinding type mill, or the metallic copper particles may be mixed at the same time when the metallic copper particles are ground.

Next, a metallic copper-containing film for an electrode, a wiring pattern, design and decorative coating films, and the like using the metallic copper dispersion liquid according to the present invention will be described. The metallic copper-containing film is a film in which metallic copper is fixed on a base material. In addition, the metallic copper-containing film in which the metallic copper particles are more firmly fixed can be obtained by adding a curable resin to the dispersion liquid. Moreover, by applying the heat to the coating film or irradiating the coating film with light or plasma, the metallic copper particles are molten and bonded, and can be fixed still more firmly. In such a metallic copper-containing film, the thickness, size, shape, and the like are not limited, the film thickness may be thin or thick, and the whole surface of the base material or one part thereof may be covered with the metallic copper-containing film. Alternatively, the metallic copper-containing film may have a fine line shape formed on one part of the base material, a broad line shape, or a fine dot shape. As the specific applications, the metallic copper-containing film can be used for an electrode and a wiring pattern by making use of conductivity of metallic copper, and can also be used for decoration applications and antimicrobial applications by making use of tone of color and antimicrobial action of metallic copper.

A decorative article and an antimicrobial article according to the present invention are obtained by forming the metallic copper-containing film on at least part of the surface of a base material, and a metal color tone or antibacterial properties of the metallic copper particle are given to the surface of the base material of the decorative article and the antimicrobial article. The whole surface of the base material can be colored to impart a metal color tone or antibacterial properties, and besides, design, a mark, and a logo mark can be formed on part of the surface of the base material, or other characters, figures, and symbols can also be formed. As the base material, inorganic materials such as metal, glass, ceramics, rock, and concrete, organic materials such as rubber, plastics, paper, wood, leather, fabric, and fiber, and a material in combination with an inorganic material and an organic material or a composite material of an inorganic material and an organic material can be used. Antibacterial properties can be also given by decorating such base materials made of the above materials by forming the metallic copper-containing film on a raw material base material before processing the base material into an article to be used, or antibacterial properties can be also given by decorating all articles after processing the base material. Moreover, giving the antibacterial properties also includes decoration of the surface of an article coated in advance on the surface of those base materials.

Specific examples of the articles giving the decoration or antibacterial properties include:

(1) exterior and interior of transportation such as automobiles, tracks, and buses, a bumper, a doorknob, a rearview mirror, a front grille, a reflecting plate of a lamp, a display instrument, and the like;

(2) exterior of electric appliances such as a television set, a refrigerator, a microwave oven, a personal computer, a mobile phone, and a camera, a remote control, a touch panel, a front panel, and the like;

(3) exterior of buildings such as houses, buildings, department stores, stores, shopping malls, pachinko parlors, wedding halls, funeral halls, shrines, and temples, window glass, an entrance, a doorplate, a gate, a door, a doorknob, a show window, interior, and the like;

(4) house facilities such as lighting equipment, furniture, furnishings, toilet equipment, Buddhist altars and fittings, a Buddha statue, and the like;

(5) utensils such as hardware and tableware;

(6) vending machines of beverage, tobacco, and the like;

(7) containers for synthetic detergents, skin care products, soft drinks, alcoholic beverages, confectionery, food products, tobacco, and pharmaceuticals;

(8) packing materials such as wrapping paper and a carton box;

(9) outfits and accessories such as clothes, shoes, bags, glasses, artificial nails, artificial hair, and jewels;

(10) sporting goods such as a baseball bat, and a golf club, and products for hobbies such as fishing tools;

(11) stationery such as pencils, colored paper, notebooks, and postcards for New Year's greetings, and business equipment such as desks and chairs; and

(12) covers and bands for books, toys such as dolls and small toy cars, cards such as a commuter pass, and recording media such as CDs and DVDs. Moreover, human nails, skin, eyebrows, hair, and the like can be used as a base material.

Next, the present invention is a process for producing a metallic copper-containing film wherein the metallic copper dispersion liquid is used. Step (a) in the production process according to the present invention is the step of adhering the metallic copper dispersion liquid on the surface of the base material. Step (b) is the step of heating the metallic copper-containing film produced in the step (a) under a reducing gas atmosphere. Step (c) is the step of irradiating the whole or one partial region of the metallic copper-containing film with light after the step (a). Moreover, step (d) is the step of irradiating the whole or one partial region of the metallic copper-containing film with plasma after the step (a). Further, step (e) is the step of removing the metallic copper-containing film in the region which was not irradiated after the step (c) or (d). Furthermore, step (f) is the step of transferring the metallic copper-containing film obtained through the steps (a) to (d) on another base material. The metallic copper-containing film can also be produced in the step (a), and the subsequent steps (b) to (f) are a step performed when necessary. A firm metallic copper-containing film can be produced by performing any one of the steps (b) to (f), and moreover, by performing the step (f), the metallic copper-containing film can be easily produced directly on a base material on which the metallic copper-containing film is difficult to form. Moreover, when an electrode and a wiring pattern are produced, it is also possible to perform any combination of steps (b) to (f) after the step (a), however it is more preferable that the step (a) is performed by an ink jet printing.

<Step (a)>

The metallic copper dispersion liquid according to the present invention is adhered (hereinafter, typically described as "coated") on the base material. As the coating of the metallic copper dispersion liquid, a general-purpose printing or transfer method such as, for example, a screen printing, a gravure printing, a flexographic printing, an ink jet printing, or an offset printing, or a general-purpose coating method using a spray, a slit coater, a curtain coater, a bar coater, a brush, a pen brush, or a spin coater can be used. The thickness of the coated layer is not particularly limited, and can be arbitrarily selected according to the purpose of use and application, however, a thickness of 0.001 to 100 μm is preferable, and a thickness of 0.005 to 70 μm is more preferable. As a coating pattern at this time, the metallic copper dispersion liquid can be coated on the whole surface of the base material, or can be coated in patterns or in figurations. According to the coating method, the purpose of use and application, the particle diameter of the metallic copper particles, the kind of the polymeric dispersant, the organic solvent, and other compounds can be arbitrarily selected. Similarly, the viscosity of the dispersion liquid and the concentration of metallic copper can be arbitrarily selected.

The metallic copper dispersion liquid according to the present invention has characteristics of a low viscosity and a high concentration, and therefore can be used particularly suitably for an ink jet printing, a spray coating, and the like. The ink jet printing is a method for forming a pattern of a predetermined shape by discharging droplets of the dispersion liquid from fine nozzles to impact the droplets on the base material. By use of this method, a computer such as a personal computer is connected to an ink jet printer, and a relative position of a nozzle as an outlet of the metallic copper dispersion liquid and the base material is changed according to graphic information inputted into the computer so that the dispersion liquid can be discharged to an arbitrary place, and thereby a desired pattern can be drawn on the base material. Moreover, the thickness and width of the metallic copper-containing film to be formed can be adjusted by a diameter of the nozzle, the amount of the dispersion liquid to be discharged, and a relative relationship between a moving speed of the nozzle and that of the base material on which a discharged substance is formed. For this reason, a fine metallic copper-containing film can be produced, and a metallic copper-containing film can be formed at a desired place by accurate discharge even on a base material having a large area whose one side exceeds 1 to 2 m. Further, the yield can be improved because disalignment with adjacent film patterns does not occur, and furthermore loss of the metallic copper dispersion liquid can be reduced because the dispersion liquid can be applied only to a necessary portion. There are various types in the ink jet printing according to a method of discharging the metallic copper dispersion liquid, for example, there are a piezoelectric device type, a bubble jet (registered trade-mark) type, an air stream type, an electrostatic induction type, an acoustic ink print type, an electrorheological ink type, and an continuous jet type, and the type of the ink jet printing can be arbitrarily selected according to a shape and thickness of a pattern, the kind of the metallic copper dispersion liquid, and the like.

In the ink jet printing, the viscosity of the metallic copper dispersion liquid is preferably 100 mPa·s or less, and more preferably 1 to 20 mPa·s, and the reason is because the above-mentioned outlet nozzle can discharge the dispersion liquid smoothly without clogging. While the particle diameter of the metallic copper particles depends on the diameter of the nozzle, a desired pattern shape, and the like, the particle diameter of 1 to 200 nm is preferable in order to prevent the nozzle from clogging or produce a high-definition pattern, and the particle diameter of 1 to 100 nm is more preferable.

As the base material, glasses such as alkali-free glass, quartz glass, crystallized clear glass, Pyrex (registered trademark) glass, and sapphire glass; inorganic materials such as $Al_2O_3$, $MgO$, $BeO$, $ZrO_2$, $Y_2O_3$, $CaO$, and GGG (gadolinium/gallium/garnet); acrylic resins such as PET (polyethylene terephthalate), PEN (polyethylene naphthalate), polypropylene, polycarbonate, and polymethyl methacrylate; vinyl chloride resins such as polyvinyl chloride and vinyl chloride copolymers, organic materials such as epoxy resins, polyarylates, polysulfones, polyethersulfones, polyimides, fluororesins, phenoxy resins, polyolefin resins, nylons, styrene resins, and ABS resins; and a substrate formed by using a composite material in which inorganic particles having a diameter of several nanometers are dispersed in the organic material; a silicon wafer; and a metal plate, and the like can be used. The base material can be arbitrarily selected from these materials according to its applications, and used as a flexible base material in a film form and the like or a rigid base material. In addition, the size of the base material is not limited, the shape of the base material may be any shape such as a disc shape, a card shape, and a sheet-like shape, and the surface of the base material does not need to be planar, and may have depressions and projections, or may have a curved surface.

On the base material, a foundation layer may be provided for the purposes of improving the planarity of the surface of the base material, enhancing the adhesive strength, preventing the deterioration of the metallic copper-containing film, and the like. Examples of the materials of the foundation layer include polymer materials such as polymethyl methacrylate, acrylic acid-methacrylic acid copolymers, styrene-maleic anhydride copolymers, polyvinyl alcohols, N-methylolacrylamide, styrene-vinyltoluene copolymers, chlorosulfonated polyethylenes, nitrocellulose, polyvinyl chloride, polyvinylidene chloride, chlorinated polyolefins, polyesters, polyimides, vinyl acetate-vinyl chloride copolymers, ethylene-vinyl acetate copolymers, polyethylenes, polypropylenes, and polycarbonates; thermosetting resins, photocurable or electron beam curable resins; and surface modifiers such as coupling agents. As the material of the foundation layer, materials having the high adhesion of the base material to the metallic copper-containing film are preferable, and specifically, thermosetting, photocurable or electron beam curable resins, and surface modifiers such as coupling agents (for example, silane coupling agents, titanate coupling agents, germanium coupling agents, and aluminum coupling agents), colloidal silica, and the like are preferable.

The foundation layer can be formed by dissolving or dispersing the above material in an appropriate solvent to prepare a coating liquid, and then coating the coating liquid on the surface of the base material according to a coating method such as a spin coating, dip coating, extrusion coating, bar coating, or the like. In general, the layer thickness (at the drying) of the foundation layer is preferably 0.001 to 20 μm, and more preferably 0.005 to 10 μm.

When necessary, a film after the metallic copper dispersion liquid is coated thereon may be heated at an appropriate temperature to evaporate and remove (hereinafter, described as "to dry by heating" or "drying by heating") the organic solvent (depending on the kind thereof, other low-boiling point compounds are included) in the metallic copper-containing film. Although the temperature to dry by heating can be arbitrarily set, the temperature of 150° C. or less is preferable in order to suppress oxidization of metallic copper, and the temperature of 120° C. or less is more preferable. The heating time can also be arbitrarily set. Also, the atmosphere can be arbitrarily set, and the heating can be also performed under an inert gas atmosphere, a reducing gas atmosphere, or an oxygen gas-containing atmosphere (in the air, or the like). $N_2$ gas, Ar gas, He gas, and the like can be used as an inert gas. In addition, the method of evaporating and removing the organic solvent or the like is not limited to the method of drying by heating, and an air-drying method or a reduced pressure drying method may be used to evaporate and remove it. In the case of the reduced pressure drying method, it is performed under the pressure lower than the atmospheric pressure. Specifically, the reduced pressure drying method may be performed under the vacuum pressure or under the ultra-vacuum pressure.

<Step (Pre-b): Preliminary Step for Step (b)>

After the step (a), it is preferable to heat the metallic copper-containing film at an appropriate temperature when necessary. By heating, the organic compounds contained in the metallic copper-containing film, such as the gelatin and the polymeric dispersant can be decomposed and/or vaporized (hereinafter, described as "heating oxidization sintering"). It is preferable to perform the heating under an oxygen-containing atmosphere in order to accelerate decomposition and/or vaporization of the organic compounds, and is more preferable to perform this heating in an oxygen-containing gas stream. The concentration of oxygen in the atmosphere is preferably 10 to 10000 ppm because the oxidization of the metallic copper particles does not progress so fast. The temperature of the heating oxidization sintering can be arbitrarily set depending on the kind of the base material or the like, however the temperature of 100 to 500° C. is preferable, and the temperature of 120 to 300° C. is more preferable. Also, the heating time can be arbitrarily set, and the heating time of, for example, about 10 minutes to about 48 hours is appropriate.

<Step (b)>

The copper-containing film is heated at an appropriate temperature under a reducing gas atmosphere (hereinafter, described as "heating reduction sintering"). In addition, it is desirable that the atmosphere is in a reducing gas stream. In this step, the reduction reaction of the copper oxide formed in the previous step such as the step (Pre-b) or the like to metallic copper is performed, and fusion of metallic copper particles is caused. This is because the metal particles of nano size used in the present invention have the melting point lower than the melting point of the bulk due to its size effect, and therefore is molten even in a relatively low temperature range. As a result, in the step in a short time, the electric resistance can be remarkably reduced and the metal color tone can be improved. For example, $H_2$ gas, CO gas, and the like can be used as a reducing gas, and the $N_2$ gas that contains about 0.1 to 5% of $H_2$ gas is preferable in terms of safety and availability. The heating temperature can be arbitrarily set depending on the kind of the base material or the like, however the heating temperature of 100 to 500° C. is preferable, the heating temperature of 120 to 300° C. is more preferable, and a temperature of the heating temperature in the step (Pre-b) to 300° C. is still more preferable. Also, the heating time can be arbitrarily set, and the heating temperature of, for example, about 10 minutes to 48 hours is appropriate. By this heating step, a volume resistance value of the obtained metallic copper-containing film can be made at order of $10^{-5}$ Ω·cm or less.

The step of evaporating and removing the organic solvent, performed when necessary, the step (Pre-b) of the heating oxidization sintering, and the step (b) of the heating reduction sintering may be separately performed, or may be continuously performed. Moreover, the ways to perform these steps are not limited to the case of performing the step of the heating oxidization sintering after the step of drying by heating. For example, the step of the heating oxidization sintering can be performed after an air drying or reduced pressure drying without performing the step of drying by heating, or in the step of the heating oxidization sintering, the organic solvent can be evaporated and removed while performing the step of the drying by heating. These steps do not need to be clearly distinguished.

<Step (c)>

The whole or one partial region of the metallic copper-containing film produced in the step (a) is irradiated with light. The light may be infrared rays, visible rays, ultraviolet rays, X-rays (soft X-rays to hard X-rays), a laser beam that radiates by amplifying light, or sunlight. A pattern is drawn on the base material by moving a light source or the base material while irradiating the metallic copper-containing film with the light. The pattern can be also drawn on the base material by converging a laser beam oscillated with a laser oscillator, arbitrarily setting a diameter of irradiation, and moving a laser mount section or the base material while irradiating the metallic copper-containing film with the laser beam. The light is absorbed by the metallic copper-containing film, the organic compounds such as the gelatin and the polymeric dispersant are decomposed and/or vaporized by the heat generated thereby, the metallic copper particles are fused, and as a result, the electric resistance of an irradiated portion of the metallic copper-containing film can be reduced and a metal color tone thereof can be improved. The nano-size fine particles have the melting point lower than the melting point of the bulk due to its size effect, and thus the pattern can be drawn with a relatively low energy and at a high speed.

According to kinds and amounts of the gelatin blended, the polymeric dispersant, the complexing agent, and the like which are used, a wavelength of the light can be arbitrarily selected in a range where the metallic copper-containing film can absorb the light, and the light with a wavelength in a ultraviolet region, a visible light region, an infrared region, or the like is preferable because of being easy to use. The light sources that emit incandescent light, discharge light, electroluminescence, or the like can be used as the light source, and an incandescent lamp, light sources that make use of luminescence by discharge such as an infrared lamp, a visible light lamp, an ultraviolet lamp, a mercury lamp, and xenon lamp, semiconductor devices (light emitting diodes) and the like that emit light when a voltage is applied, such as LED can be used as the light source. The typical lasers include: semiconductor lasers using GaN, GaAsAl, InGaAsP, or the like; excimer lasers using ArF, KrF, XeCl, or the like; dye lasers using rhodamine, or the like; gas lasers using He—Ne, He—Cd, $CO_2$, Ar ion, or the like; free electron lasers; solid state lasers such as ruby lasers and Nd: YAG lasers; and so on. Moreover, a higher order harmonic wave such as a second harmonic wave and third harmonic wave of these lasers may be also used, and a laser beam at any wavelength in the ultraviolet region, the visible light region, and the infrared region can be used. Further, irradiation of a continuous wave or irradiation of a pulse wave may be used. Conditions on applied energy such as a diameter of irradiation of the light, a scan speed, and an output can be arbitrarily set in a range in which the oxidization of metallic copper, and ablation and peeling of the metallic copper-containing film do not occur. The diameter of irradiation can be arbitrarily set in accordance with a pattern or figure to be drawn, and the diameter of irradiation of 10 μm to 5 mm is preferable. The scan speed can also be arbitrarily set according to other parameters, required accuracy, manufacturing capacity, and the like.

The atmosphere under which light irradiation is performed, such as an inert gas atmosphere, a reducing gas atmosphere, an oxygen gas-containing atmosphere (air atmosphere), can be arbitrarily set. By using the metallic copper dispersion liquid according to the present invention, the metallic copper-containing film having a low resistance and a good metal color tone can be formed without causing the oxidation of copper in the metallic copper-containing film even under the oxygen gas-containing atmosphere (air atmosphere), which is inferred to be attributed to the presence of the gelatin. Specifically, this can be achieved by irradiation with a continuous wave laser beam having a wavelength in the infrared region at a scan speed of 1 to 500 mm/s and at an output range of 1 to 140 W under the oxygen gas-containing atmosphere (air atmosphere). At this time, the conditions on laser irradiation are adjusted so that main peak strength in a $Cu_2O$ (111) plane can be 20 or less when main peak strength in a metallic copper (111) plane is assumed to be 100 in X-ray diffraction of the metallic copper-containing film at a portion irradiated with the laser beam. It is more preferable to set an output of the laser beam to 10 to 100 W, and it is still more preferable to set an output of the laser beam in a range of 20 to 50 W. The semiconductor lasers are preferable because of being generally suitable for irradiation with a continuous laser beam having a wavelength in the infrared region.

<Step (d)>

The whole or one partial region of the metallic copper-containing film produced in the step (a) is irradiated with plasma to produce a plasma-irradiated metallic copper-containing film. In this step, organic compounds contained in the metallic copper-containing film, such as the gelatin and the polymeric dispersant are decomposed or vaporized, and fusion of metallic copper particles is caused. The plasma irradiation can be arbitrarily selected from the known methods. For example, the metallic copper-containing film is placed in a plasma treatment apparatus, a gas is introduced, and energy is applied to ionize the gas to be in a plasma state. The excitation energy that is supplied to the gas is electric discharge, direct current, radio frequency, microwave, or electromagnetic radiation and the like. Moreover, in general, the plasma can be also generated by applying voltage between two electrodes to form an electric field. The gases suitable for plasma treatment include helium, argon, hydrogen, nitrogen, air, nitrous oxide, ammonia, carbon dioxide, oxygen, and the like, and the oxygen gas, the hydrogen gas, a mixed gas of oxygen and helium or argon, and a mixed gas of hydrogen and helium or argon are more preferable. The plasma treatment can be performed under the atmospheric conditions, or the plasma treatment may be performed in an apparatus capable of retaining the plasma under a reduced pressure or a vacuum condition. The pressure is preferably in a range of about 10 mTorr to about 760 Torr (about 1.333 to about 101325 Pa).

Specifically, the plasma treatment can be performed as described in the following example. First of all, the metallic copper-containing film is placed in a plasma treatment apparatus, and the base material is heated in the atmospheric air when necessary. Although the heating temperature can be set according to the material quality of the base material, the heating temperature is preferably 180° C. or less when a plastic having a low heat resistance is used, and more preferably 120° C. or less. As the lower limit value of the heating temperature, a temperature of about 20° C. is practical. Next, it is preferable that heating is performed under a reduced pressure or a vacuum condition. And, the heating temperature is preferably 180° C. or less, and still more preferably 120° C. or less. The heating time can be arbitrarily set. And, the gas is introduced in the plasma treatment apparatus to generate the plasma while the heating is continuously performed, and the whole or one partial region of the metallic copper-containing film is irradiated with plasma. The microwave energy having a frequency of 2450 MHz is preferably supplied to generate microwave surface wave plasma. When one partial region is irradiated with plasma, the other region can be protected so as not to be irradiated with plasma by putting a mask pattern on the metallic copper-containing film. The plasma irradiation time can be arbitrarily set, and is, for example, about 0.01 to 30 minutes, and a plasma irradiation time of about 0.01 to 10 minutes is suitable. The plasma irradiation can be performed in two stages, and the metallic copper-containing film is irradiated with plasma in the presence of oxygen gas to decompose an organic compound such as the gelatin in the first step, and thereafter the metallic copper-containing film is irradiated in the presence of a reducing gas in the second step, and thereby the metallic copper particles can be sintered.

<Step (e)>

Further, an unnecessary part of the metallic copper-containing film, or a part thereof which is not irradiated with the light in the step (c) or a part thereof which is not irradiated with the plasma in the step (d) may be removed using an appropriate solvent when necessary. As the solvent, various solvents such as alcohol solvents, glycol ether solvents, and aromatic solvents can be used. The unnecessary part or the like can be removed by immersing the base material in such a solvent or by wiping off it with fabric or paper dipped in the solvent.

<Step (f)>

Next, the whole or one partial region of the metallic copper-containing film produced on the base material can be also transferred onto another base material after the step (a), the step (b), the step (c), the step (d), or the step (e).

In addition, the steps (b) to (e) after the step (a) can be arbitrarily combined and performed. For example, the step (b) can be performed after the step (a), and the step (c) can further be performed, or the step (c), the step (d), or the step (e) can be performed after the step (a), and the step (b) can further be performed. Moreover, in the step (b), only the step (Pre-b) or only the step (b) can be combined and performed. For example, the step (c) can be performed after the step (a), and the step (b) can further be performed.

It is preferable that the whole of the metallic copper-containing film produced by any one of (a) to (f) in the present invention is sintered because the resistance value is low, and thus it is preferable to perform the heating, light irradiation, or plasma irradiation for the sufficient time and with the sufficient strength. However, only the surface part of the metallic copper containing film may be sintered and the inside thereof may not be sintered, and there is no problem even when only one part of the surface is sintered as long as the performances of the resistance value or the like, needed to use can be obtained. The volume resistance value of the metallic copper-containing film is preferably 50 µΩ·cm or less, more preferably 20 µΩ·cm or less, and still more preferably 10 µΩ·cm or less. The thickness, size, shape, and the like of such a metallic copper-containing film are not limited, and the metallic copper-containing film may be a thick film or a thick film, and the film may cover the whole or part of the base material. Alternatively, the metallic copper-containing film may have a fine wire-like shape or wide wire-like shape formed on one part of the base material, or may have a fine dotted shape. For example, the thickness is preferably 1 µm or less, and more preferably 0.5 µm or less. As specific applications, the metallic copper-containing film can be used in an electrode and a wiring pattern making use of the electronic conductivity of metallic copper, and can be also used for decoration applications and antibacterial applications making use of the color tone or antibacterial properties of the metallic copper.

EXAMPLES

Hereinafter, the present invention will be described in more detail illustrating the Examples, however the present invention is not limited to these Examples.

Examples 1 to 10

To 150 ml of pure water, 24 g of industrial copper(II) oxide (N-120 manufactured by NC-Tech Co., Ltd.) and 2.8 g of gelatin (amine value of 23, acid value of 29, amine value −acid value=−6, and mass average molecular weight of 190,000) as protective colloid were added and mixed, and after the pH of the mixed solution was adjusted at 11 using 15% aqueous ammonia, the temperature of the mixed solution was raised from room temperature to 90° C. in 20 minutes. After the temperature was raised, a solution prepared by mixing 0.24 g of a 1% 3-mercaptopropionic acid solution as a complexing agent and 10 g of 80% hydrazine monohydrate to 150 ml of pure water was added to the mixed solution under stirring, and the resultant mixture was reacted with copper oxide for 1 hour to produce copper particles coated with the gelatin. Thereafter, the copper particles were subjected to filtration and washing until a specific conductivity of a filtrate reached 100 µS/cm or less, and dried for 10 hours at a temperature of 60° C. under an atmosphere of nitrogen gas to obtain the metallic copper particles coated with the gelatin.

Each of the metallic copper dispersion liquids (Samples A to J, and concentration of metallic copper particles is 50% by mass) according to the present invention was obtained by the following steps: mixing and suspending 20 g of the metallic copper particles which are coated with the gelatin and has an average particle diameter of 50 nm, synthesized according to the above method and 20 g of toluene in which 1.5 g of a polymeric dispersant was dissolved; and then dispersing the resultant mixture with a paint shaker for 1 hour. Amine values, glass transition points, and specific heat capacities of the polymeric dispersants used herein are shown in Table 1. In addition, each of the polymeric dispersants used in the dispersion liquids A, C to J was a straight-chain type acrylic polymer or a straight-chain type acrylic copolymer, the polymeric dispersant used in the dispersion liquid B was a comb-shaped acrylic polymer, and the mass average molecular weight of any of these polymeric dispersants was in a range of 5000 to 10000 g/mol.

The particle size distributions of the metallic copper particles in the obtained metallic copper dispersion liquids were measured with a dynamic light scattering method particle size distribution measuring apparatus (Microtrack UPA Type: manufactured by Nikkiso Co., Ltd.), and the results of the particle size distributions of the metallic copper particles blended in the metallic copper dispersion liquids according to the present invention were as shown in Table 1. The solvent slurries prepared by adjusting the concentration so as to become 0.1 to 0.2 of the signal intensity of laser were used for the dynamic light scattering method particle size distribution measurement.

Example 11

Metallic copper particles (average particle diameter of 50 nm) coated with a collagen peptide were obtained in the same manner as in Example 1 except that a cattle-derived high-quality collagen peptide ((amine value−acid value) of 0 or less, molecular weight of about 3000 to 5000, and product name: Nippi Peptide DV manufactured by Nippi, Inc.) was used in place of the gelatin used as protective colloid in Example 1, and subsequently a metallic copper dispersion liquid (sample K, and concentration of metallic copper particles is 50% by mass) according to the present invention was obtained in the same manner as in Example 1.

The measurement results of the particle size distribution of the sample K measured by the same method as that for the sample A are shown in Table 1.

TABLE 1

| | | Physical properties of dispersant | | | Particle size distribution | | | | |
| | | | | | 10% | 50% | 90% | | |
| Example | Dispersion liquid | Amine value [mg KOH/g] on polymer | Glass transition point [° C.] | Specific heat capacity [J/(g · K)] | Cumulative particle diameter [nm] | Cumulative particle diameter [nm] | Cumulative particle diameter [nm] | SD | Viscosity [mPa · s] |
|---|---|---|---|---|---|---|---|---|---|
| 1 | A | 45 | −8.7 | 1.77 | 58 | 94 | 169 | 1.2 | 1.9 |
| 2 | B | 18 | −65.7 | 1.61 | 47 | 83 | 200 | 1.8 | 1.9 |
| 3 | C | 24 | −52.8 | 1.68 | 44 | 74 | 158 | 1.5 | 2.6 |
| 4 | D | 47 | −56.5 | 1.77 | 41 | 67 | 151 | 1.6 | 3.5 |
| 5 | E | 29 | −43.6 | 1.58 | 44 | 75 | 156 | 1.5 | 4.3 |
| 6 | F | 61 | −39.7 | 1.48 | 42 | 71 | 153 | 1.6 | 2.6 |
| 7 | G | 90 | −21.9 | 1.76 | 64 | 116 | 252 | 1.6 | 2.0 |
| 8 | H | 70 | 3.1 | 1.81 | 44 | 75 | 205 | 2.1 | 1.9 |
| 9 | I | 120 | 6.6 | 1.71 | 56 | 104 | 277 | 2.1 | 2.0 |
| 10 | J | 25 | −57.7 | 1.40 | 45 | 75 | 141 | 1.3 | 1.9 |
| 11 | K | 45 | −8.7 | 1.77 | 55 | 74 | 139 | 1.1 | 2.0 |

Comparative Examples 1 to 3

Metallic copper dispersion liquids (Samples L to N and concentration of metallic copper particles was 50% by mass) were obtained by the following steps: mixing and suspending 20 g of the metallic copper particles (50 nm) coated with the gelatin, used in Example 1 and 20 g of toluene in which 1.5 g of a polymeric dispersant was dissolved; and then dispersing the resultant mixture with a paint shaker for 1 hour. The amine values, glass transition points, and specific heat capacities at the glass transition points of the polymeric dispersants, used herein are shown in Table 2. In addition, each polymeric dispersant was a straight-chain type acrylic polymer or a straight-chain type acrylic copolymer, and the mass average molecular weights of the polymeric dispersants were in a range of 5000 to 10000 g/mol.

The particle size distributions of the metallic copper particles in the obtained metallic copper dispersion liquids were measured with a dynamic light scattering method particle size distribution measuring apparatus (Microtrack UPA Type: manufactured by Nikkiso Co., Ltd.) in the same manner as in Examples 1-11, and the results of the particle size distributions of the metallic copper particles were as shown in Table 2.

TABLE 2

| | | Physical properties of dispersant | | | Particle size distribution | | | | |
| | | | | | 10% | 50% | 90% | | |
| Comparative Example | Dispersion liquid | Amine value [mg KOH/g] on polymer | Glass transition point [° C.] | Specific heat capacity [J/(g · K)] | Cumulative particle diameter [nm] | Cumulative particle diameter [nm] | Cumulative particle diameter [nm] | SD | Viscosity [mPa · s] |
|---|---|---|---|---|---|---|---|---|---|
| 1 | L | 120 | 3.0 | 1.93 | 76 | 139 | 258 | 1.3 | 1.8 |
| 2 | M | 90 | 16.1 | 1.76 | 76 | 147 | 331 | 1.7 | 2.1 |
| 3 | N | 120 | −1.2 | 1.79 | 66 | 135 | 333 | 2.0 | 1.5 |

Production of Metallic Copper-Containing Films by Heating

Next, production of metallic copper-containing films was tried using the metallic copper dispersion liquids produced in the above Examples and Comparative Examples.

First of all, each sample of the metallic copper dispersion liquids in the above Examples and Comparative Examples was dropped on a polyimide substrate (manufactured by Du Pont-Toray Co., Ltd., a Kapton (registered trade-mark) film 300V type, thickness of 75 μm), and spread on the base material with a bar coater (#6) so that the metallic copper dispersion liquid can have a uniform thickness (about 14 μm), and thereafter the solvent was vaporized in an $N_2$ gas atmosphere by heating the base material at 80° C. for 1 hour to produce a metallic copper-containing the coating film.

Next, the pre-heating of each sample was performed at 200° C. in an atmosphere where the concentration of oxygen was controlled to 10 ppm, and thereafter the sintering was performed at 200° C. in a 3% hydrogen atmosphere to obtain a conductive film. The volume resistance values for the obtained conductive films were measured and the states of the metallic copper-containing films were visually observed. A Loresta GP Type low resistivity meter (manufactured by Mitsubishi Chemical Co., Ltd.) was used for the measurement of volume resistance values. Any of the metallic copper-containing films in Examples exhibited the low specific resistance value, and any of the appearances thereof showed metallic color tone.

TABLE 3

| | Dispersion liquid | Specific resistance value [μΩ · cm] |
|---|---|---|
| Example 1 | A | 13.3 |
| Example 2 | B | 12.3 |
| Example 3 | C | 25.7 |
| Example 4 | D | 28.3 |
| Example 5 | E | 24.6 |
| Example 6 | F | 35.9 |
| Example 7 | G | 28.0 |
| Example 8 | H | 16.9 |
| Example 9 | I | 24.6 |
| Example 10 | J | 20.6 |
| Example 11 | K | 17.8 |
| Comparative Example 1 | L | 83.9 |

TABLE 3-continued

| | Dispersion liquid | Specific resistance value [μΩ · cm] |
|---|---|---|
| Comparative Example 2 | M | 110 |
| Comparative Example 3 | N | 118 |

Production of Metallic Copper-Containing Films by Plasma Sintering

The metallic copper dispersion liquid (dispersion (A)) was applied on a polyimide film (manufactured by Du Pont-Toray Co., Ltd., a Kapton (registered trade-mark) film 300V type, thickness of 75 μm) with a bar coater (#3) to produce a metallic copper-containing film. Thereafter, the plasma treatment was performed using Micro Labo-PS manufactured by Nissin Inc. to obtain a metallic copper-sintered film in the following manner.

First of all, a metallic copper-containing film was placed on a stage heated at a predetermined temperature of 100° C. in a plasma apparatus and heated for a predetermined time of 180 seconds. Thereafter, the pressure in the apparatus was reduced for 60 seconds, 3% $H_2$—He gas was filled in the apparatus for 30 seconds, and the plasma irradiation was performed. After the plasma treatment, cooling was performed by purging $N_2$ gas for 90 seconds to obtain a metallic copper-sintered film. The obtained metallic copper-containing film exhibited a low specific resistance value, and the appearance thereof showed metallic color tone.

TABLE 4

| Example | Dispersion liquid | Sintering temperature [° C.] | Specific resistance value [μΩ · cm] |
|---|---|---|---|
| 1 | A | 100 | 5.1 |

Production of Metallic Copper-Containing Film by Photo Sintering

The metallic copper dispersion liquid (dispersion (A)) was coated on a polyimide film (manufactured by Du Pont-Toray Co., Ltd., a Kapton (registered trade-mark) film 300V type, thickness of 75 μm) with a bar coater (#3) to produce a metallic copper-containing film. Thereafter, the light irradiation was performed with a xenon lamp irradiation apparatus Sinteron 2000 manufactured by Xenon Co., Ltd. under the conditions (voltage, output energy, and irradiation time) as described in Table 5 to obtain a metallic copper-sintered film. The obtained metallic copper-containing film exhibited a low specific resistance value, and the appearance thereof showed metallic color tone.

TABLE 5

| Example | Dispersion liquid | Substrate | Voltage [V] | Output energy [J] | Irradiation time [ms] | Specific resistance value [μΩ · cm] | Film thickness [μm] |
|---|---|---|---|---|---|---|---|
| 1 | A | Polyimide film | 2500 | 1438 | 2.0 | 28.1 | 0.6 |
| | | PEN film | 2200 | 1113 | 2.0 | 49.5 | 1.1 |
| | | PET film | 3800 | 830 | 0.5 | 67.4 | 1.7 |

INDUSTRIAL APPLICABILITY

The metallic copper dispersion liquid according to the present invention can maintain dispersion stability of the metallic copper particles in the organic solvent for a long period of time and maintain dispersion stability after the metallic copper dispersion liquid is prepared until it is used, and accordingly, the metallic copper dispersion liquid according to the present invention has an excellent coating suitability, and can be applied to a wide range of coating methods such as an ink jet printing and a spray coating. Moreover, the composition of a paint, an ink, a paste, or the like can be arbitrarily designed by blending resin components andthe like according to the purpose of use.

By using the metallic copper dispersion liquid according to the present invention, the metallic copper-containing film can be also produced by heating at a relatively low temperature or by light irradiation, and the metallic copper-containing film can be widely used for materials in which electrical conduction is ensured and materials to which antistatic properties, electromagnetic interference shielding properties, a metal color tone, antibacterial properties, or the like is given, particularly, the metallic copper-containing film can be also used for new applications in nanotechnology, such as formation of an electrode and a circuit-wiring pattern, actively developed in recent years, and moreover the metallic copper-containing film can be also applied to applications alternative to plating techniques, such as the provisions of designability or decorativeness due to metal color tone and antibacterial properties.

The invention claimed is:

1. A metallic copper dispersion liquid comprising at least metallic copper particles having a gelatin on surfaces thereof, a polymeric dispersant, and an organic solvent, wherein
the polymeric dispersant has an amine value of 18 to 61 mgKOH/g, a glass transition point within a range of −65.7 to −8.7° C., and a specific heat capacity of 1.40 to 1.77 J/(g·K) at a glass transition point of the polymeric dispersant, and
the metallic copper particles have, in the dispersion liquid, a 50% cumulative particle diameter (D50) of 67 to 94 nm and a 90% cumulative particle diameter (D90) of 139 to 200 nm, wherein the gelatin on the surfaces of the metallic copper particles comprises a collagen peptide having a molecular weight of 3000 to 5000.

2. The metallic copper dispersion liquid according to claim 1, wherein the metallic copper particles have a 10% cumulative particle diameter (D10) of 41 to 58 nm.

3. The metallic copper dispersion liquid according to claim 1, wherein the polymeric dispersant is a straight-chain type acrylic polymer or a straight-chain type acrylic copolymer.

4. The metallic copper dispersion liquid according to claim 1, wherein the polymeric dispersant has a mass average molecular weight of 1000 to 100000 g/mol.

5. The metallic copper dispersion liquid according to claim 1, wherein the metallic copper particles have an SD value of 0.6 to 3.5, wherein
the SD value is calculated from the values of a 10% cumulative particle diameter (D10), the 50% cumulative particle diameter (D50), and the 90% cumulative particle diameter (D90) using the following equation 1

$$SD \text{ value} = (D90 - D10)/D50 \quad \text{Equation 1.}$$

6. The metallic copper dispersion liquid according to claim 1, wherein the organic solvent is at least one selected from the group consisting of hydrocarbons, alcohols, ketones, esters, ethers, glycols, glycol ethers, and glycol esters.

7. The metallic copper dispersion liquid according to claim 1, wherein the polymeric dispersant is blended in an amount of 0.1 to 20 parts by mass based on 100 parts by mass of the metallic copper particles.

8. The metallic copper dispersion liquid according to claim 1, having a viscosity of 100 mPa·s or less.

9. The metallic copper dispersion liquid according to claim 1, having a concentration of the metallic copper particles of 15% by mass or more and a viscosity of 100 mPa·s or less.

10. A process for preparing a metallic copper dispersion liquid, comprising the steps of:
reducing a copper oxide in the presence of a gelatin in an aqueous solvent, wherein the gelatin comprises a collagen peptide having a molecular weight of 3000 to 5000;
thereafter performing a solid-liquid separation; and
subsequently mixing and dispersing metallic copper particles having the gelatin on surfaces thereof, obtained by the solid-liquid separation with a polymeric dispersant in an organic solvent; wherein
the polymeric dispersant has an amine value of 18 to 61 mgKOH/g, a glass transition point within a range of −65.7 to −8.7° C., and a specific heat capacity of 1.40 to 1.77 J/(g·K) at a glass transition point of the polymeric dispersant, and
the metallic copper particles have a 50% cumulative particle diameter (D50) of 1 to 130 nm and a 90% cumulative particle diameter (D90) of 10 to 300 nm.

11. The process for preparing a metallic copper dispersion liquid according to claim 10, wherein the polymeric dispersant is a straight-chain type acrylic polymer or a straight-chain type acrylic copolymer.

12. The process for preparing a metallic copper dispersion liquid according to claim 10, wherein the polymeric dispersant has a mass average molecular weight of 1000 to 100000 g/mol.

13. An electrode formed using the metallic copper dispersion liquid according to claim 1.

14. A wiring pattern formed using the metallic copper dispersion liquid according to claim 1.

15. A coating film formed using the metallic copper dispersion liquid according to claim 1.

16. A decorative article forming the coating film according to claim 15 formed on at least one part of a surface of a base material.

17. An antimicrobial article forming the coating film according to claim 15 formed on at least one part of a surface of a base material.

18. A process for producing a metallic copper-containing film, comprising a step (a) of adhering the metallic copper dispersion liquid according to claim 1 on a surface of a base material.

19. The process for producing a metallic copper-containing film, comprising a step (b) of heating the metallic copper-containing film produced by the step (a) according to claim 18 under a reducing gas atmosphere.

20. The process for producing a metallic copper-containing film, comprising a step (c) of irradiating a whole or one partial region of the metallic copper-containing film produced by the step (a) according to claim 18 with light.

21. The process for producing a metallic copper-containing film, comprising a step (d) of irradiating a whole or one partial region of the metallic copper-containing film produced by the step (a) according to claim 18 with plasma.

22. The process for producing a metallic copper-containing film, comprising a step (e) of removing the metallic copper-containing film in an unirradiated region after preforming the step (c) according to claim 20.

23. The process for producing a metallic copper-containing film, comprising a step (f) of transferring, on another base material, a whole or one partial region of the metallic copper-containing film produced on the base material by the step according to claim 18.

24. The process for producing a metallic copper-containing film, comprising a step (e) of removing the metallic copper-containing film in an unirradiated region after preforming the step (d) according to claim 21.

25. The metallic copper dispersion liquid according to claim 1, wherein the polymeric dispersant having an amine value of 61 mg KOH/g.

26. The metallic copper dispersion liquid according to claim 1, wherein the polymeric dispersant having a different between an amine value and an acid value (amine value-acid value) of 61.

* * * * *